United States Patent [19]
Munkholm

[11] Patent Number: 5,958,786
[45] Date of Patent: *Sep. 28, 1999

[54] FLUORESCENT POLYMERIC SENSOR FOR THE DETECTION OF CREATININE

[75] Inventor: Christiane Munkholm, Salem, Mass.

[73] Assignee: Bayer Corporation, E. Walpole, Mass.

[ * ] Notice: This patent is subject to a terminal disclaimer.

[21] Appl. No.: 08/906,710

[22] Filed: Aug. 5, 1997

[51] Int. Cl.$^6$ .................................................. G01N 33/00
[52] U.S. Cl. ........................... 436/98; 436/106; 436/113; 436/164; 436/169; 436/170; 436/172; 436/800; 422/55; 422/56; 422/82.05; 422/82.08; 422/82.11
[58] Field of Search .............................. 436/98, 106, 111, 436/113, 164, 169, 170, 172, 800; 422/55, 56, 82.05, 82.07, 82.08, 82.11

[56] References Cited

U.S. PATENT DOCUMENTS

| | | | |
|---|---|---|---|
| 4,223,089 | 9/1980 | Rothe et al. | 435/12 |
| 4,548,906 | 10/1985 | Sekikawa et al. | 436/113 |
| 5,005,572 | 4/1991 | Raemer | 128/207.14 |
| 5,008,078 | 4/1991 | Yaginuma et al. | 422/56 |
| 5,173,434 | 12/1992 | Morris | 436/172 |
| 5,198,335 | 3/1993 | Sekikawa et al. | 435/4 |
| 5,286,624 | 2/1994 | Terashima et al. | 435/12 |
| 5,330,868 | 7/1994 | Santilli | 430/106 |
| 5,368,027 | 11/1994 | Lubbers et al. | 600/345 |
| 5,372,784 | 12/1994 | Morris | 422/82.08 |
| 5,387,525 | 2/1995 | Munkholm | 436/111 |
| 5,506,148 | 4/1996 | Munkholm | 436/111 |
| 5,527,708 | 6/1996 | Blass | 436/98 |
| 5,577,137 | 11/1996 | Groger | 385/12 |

FOREIGN PATENT DOCUMENTS

| | | |
|---|---|---|
| 0281000 | 9/1988 | European Pat. Off. . |
| 0708335 | 4/1996 | European Pat. Off. . |

OTHER PUBLICATIONS

Wolfbeis et al. *Analytica Chimica Acta*, vol. 185, pp. 321–327, 1986.

Preininger et al. *Analytica Chimica Acta*, vol. 334, pp. 113–123, Nov. 1996.

Muller et al. *Proc. SPIE–Int. Soc. Opt. Eng.*, vol. 2388 (Advances in Fluorescence Sensing Technology II) pp. 558–567, 1995.

Campanella, Luigi et al., "Suitable Potentiometric Enzyme Sensors for Urea and Creatinine", *Analyst*, Jun. 1990, vol. 115, 827–830.

Clark, John T., "Colorimetric Determination and Distribution of Urinary Creatinine and Creatine", *Clinical Chemistry*, vol. 7, No. 4, Aug. 1961 271–283.

Fossati, Piero et al., "Enzymic Creatinine Assay: A New Colorimetric Method Based on Hydrogen Peroxide Measurement", *Clin. Chem.* 29/8 (1993) 1494–1496.

Kihara, Kunio et al. "Determination of Creatinine with a Sensor Based on Immobilized Glutamate Dehydrogenase and Creatinine Deiminase", *Analytica Chimica Acta*, 188 (1986) 75–80.

Kubo, Izumi, "Immobilization of Creatinine Deiminase on a Substituted Poly(Methylglutamate) Membrane and its Use in a Creatinine Sensor" *Analytica Chimica Acta*, 187 (1986) 31–37.

(List continued on next page.)

*Primary Examiner*—Maureen M. Wallenhorst
*Attorney, Agent, or Firm*—Arthur S. Morgenstern; Charles L. Gagnebin, III

[57] ABSTRACT

The present invention provides a creatinine sensor material having a first layer of a protonated pH sensitive fluorophore immobilized in a hydrophobic polymer, wherein the fluorophore can react quantitatively with ammonia and the transducing moiety of the fluorophore is neutrally charged when deprotonated; a second layer of creatinine deiminase and a polymer; and a third layer of a polymer. The present invention also provides a method for detecting creatinine using the creatinine sensor material and optical sensing devices that incorporate the creatinine sensor material.

34 Claims, 2 Drawing Sheets

OTHER PUBLICATIONS

Jaynes, Patrick K. et al. "An Enzymic, Reaction–Rate Assay for Serum Creatinine with a Centrifugal Analyzer", *Clin. Chem.* 28/1 (1982) 114–117.

Thompson, Huvin et al., "Ion Electrode Based Enzymatic Analysis of Creatinine", *Analytical Chemistry*, 46/2 (Feb. 1974) 246–249.

Weigl, Bernhard H. et al., "Sensitivity Studies on Optical Carbon Dioxide Sensors Based on Ion Pairing", *Sensors and Actuators*, B 28 (1995) 151–156.

Wolfbeis, Otto S. "Optical Sensing Based on Analyte Recognition by Enzymes, Carriers and Molecular Interations", *Analytica Chimica Acta*, 250 (1991) 181–201.

FLUORESCENT POLYMERIC SENSOR FOR THE DETECTION OF CREATININE

BACKGROUND OF THE INVENTION

1. Field of the Invention

The present invention relates to sensors for the detection of creatinine.

2. Description of Related Art

Continuous monitoring of creatinine can be accomplished by a number of electrochemical methods. Sensors utilizing such methods can be created by immobilizing the enzyme creatinine deiminase onto the surface of an electrode. The enzymatic hydrolysis of creatinine produces N-methylhydantoin and ammonia. At physiologic pH the ammonia is protonated to form ammonium ions, which increase the electrical conductivity of the solution proximal to the electrode.

Creatinine can also be monitored using an optical sensor. The detection of analytes by optical sensors usually requires the development of fluorescent transducers which are specific for different analytes. Optical transducers can also be coupled to the detection of creatinine via the creatinine deiminase driven hydrolysis of creatinine, with the optical transducer modulated by ammonium or ammonia.

Detection of ammonium requires an ammonium specific ionophore coupled to a chromophore that changes its absorption spectrum upon protonation, and a lipophilic anionic site. As such, sensors based on the detection of ammonium can be expensive and complex.

Detection of ammonia requires a protonated pH sensitive indicator ($INDH^+$) which changes its absorption or fluorescence spectrum upon deprotonation:

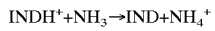

$$INDH^+ + NH_3 \rightarrow IND + NH_4^+$$

There is also a drawback to designing a sensor based on detection of ammonia: namely the rapid protonation of ammonia at physiologic pH. The $pK_a$ of ammonium is 9.3, which is not a pH that supports maximum enzyme activity.

Hydrophobic polymers, optically transparent and permeable to the analyte of interest, are used with optical sensors when the analyte is a vapor or gas and is capable of diffusion into a hydrophobic membrane. A complication arises when hydrophobic polymers are used with certain fluorescent dyes. Sensors for ammonia require a protonated indicator. When combined with a hydrophobic membrane for the detection of ammonia, polyanionic pH indicators, which are the common variety of protonated indicator and the type used in the fluorescent urea sensor described in Rhines and Arnold (*Anal. Chim. Acta,* 231: 231–235 (1990)), do not produce an activated and protonated fluorophore.

Sensors have been developed for the detection of creatinine based on enzymatic cleavage of creatinine. However, many of the sensors that have been developed for the detection of creatinine have been coupled to gas electrodes (Thompson and Rechnitz, *Anal. Chem.,* 46: 246–249 (1974); Kihara and Yasukawa, *Anal. Chim. Acta,* 183: 75–80 (1986)), unlike the present invention, which couples the enzymatic cleavage of creatinine to detection by a fluorescent polymer coating.

While various indicators for creatinine are known, many sensors exhibit problems with interferences from pH and $CO_2$ effects, low sensitivity, slow response times and reversibility. From a manufacturing standpoint, it would therefore be desirable to develop an inexpensive sensor capable of detecting creatinine that has a high sensitivity, fast response time, and is reversible. It would also be advantageous for the sensor to be able to function in conjunction with sensors detecting other analytes.

SUMMARY OF THE INVENTION

The present invention provides a creatinine sensor material comprising a first layer comprising a pH sensitive fluorophore immobilized in a first, hydrophobic polymer, wherein the fluorophore can react quantitatively with ammonia and the transducing moiety of the fluorophore is neutrally charged when deprotonated; a second layer comprising creatinine deiminase and a polymer; and a third layer comprising a polymer.

The present invention also provides a method for measuring creatinine comprising measuring the fluorescence of the creatinine sensor material; exposing the sensor material to a solution comprising creatinine; measuring the fluorescence change; and determining the concentration of the creatinine.

The present invention also provides an optical sensing device for measuring ammonia concentration in a solution comprising creatinine, comprising a first layer comprising a pH sensitive fluorophore immobilized in a first, hydrophobic polymer, wherein the fluorophore can react quantitatively with ammonia and the transducing moiety of the fluorophore is neutrally charged when deprotonated, on the surface of an optical component which is transparent to incident and emissive electromagnetic waves; a second layer comprising creatinine deiminase and a polymer on the surface of the first layer; and a third layer comprising a polymer on the surface of the second layer; wherein the optical component is optically connected to means for collecting radiant emission to measure the fluorescence indicative of ammonia concentration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
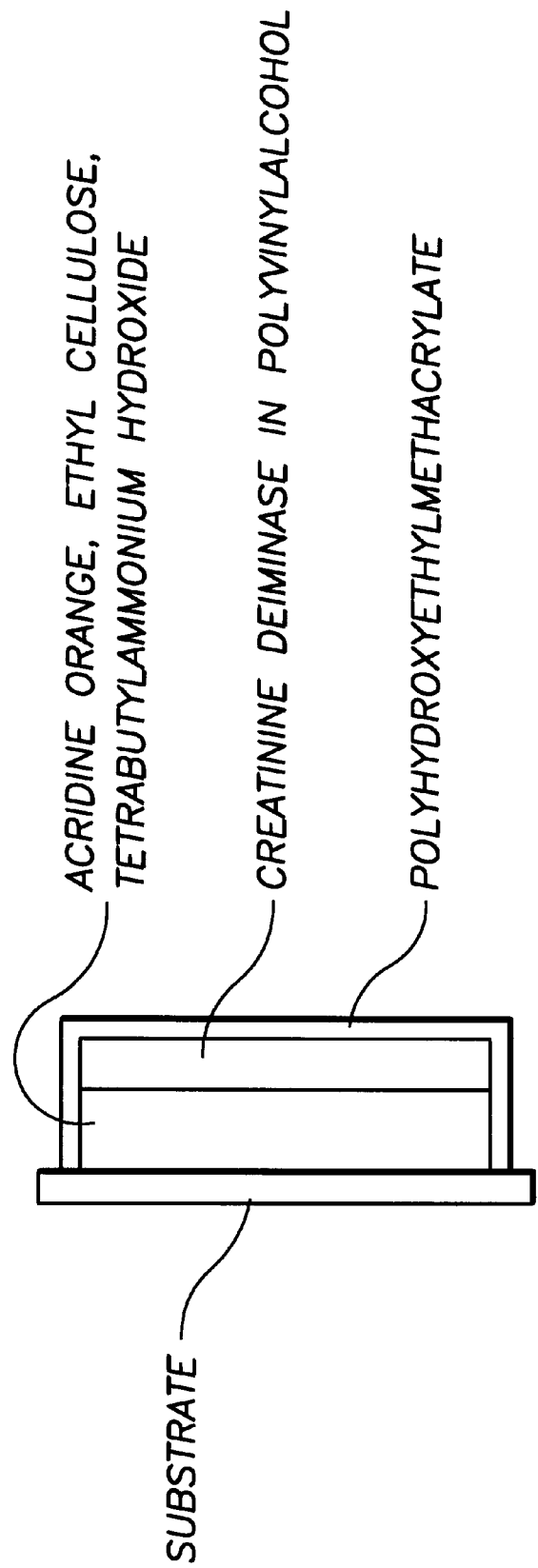
FIG. 1 shows a creatinine sensor configuration as used in Example 1.

The present invention relates to sensors for the detection of creatinine. The sensors of the present invention comprise a fluorophore immobilized in a hydrophobic polymer, wherein the fluorophore can react quantitatively with ammonia and the transducing moiety is neutrally charged when deprotonated.

The transducing moiety is the ring or group of rings in the molecular structure of the pH sensitive fluorophore, which produces the fluorescence when radiated with the particular excitation energy required for excitation. This same segment of the molecule undergoes a resonance change due to protonation and deprotonation, and this change results in a change in the fluorescence which allows one to calibrate the fluorescence as a function of pH alteration. A substituent ring that is not involved in the pH based resonance change may be negatively charged when deprotonated; see e.g. the benzoic acid residue on rhodamine.

In the present invention, the detection of creatinine in a solution depends on the presence of the enzyme creatinine deirninase, which catalyzes the following reaction:

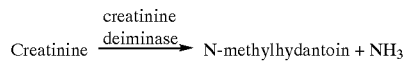

The sensors of the present invention detect ammonia that is produced in the reaction above. Detection of ammonia is based on changes in the fluorescence spectrum of the fluorophore upon deprotonation, as shown in the reaction below:

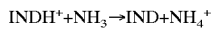

The sensor material in its simplest form comprises one layer, that of the fluorescent polymer. In such a case, creatinine deiminase is added to the solution in which creatinine is to be measured. In a preferred embodiment, the sensor material comprises three layers: a transducer layer, an enzyme layer, and a protective layer. The transducer layer is comprised of the fluorophore immobilized in a hydrophobic polymer. The enzyme layer is comprised of the enzyme creatinine deiminase immobilized in a polymer. The protective layer is another polymer.

Fluorophores suitable in the sensors of this invention are fluorescent pH indicators wherein the transducing moieties are neutrally charged when deprotonated, and which exist in the protonated state in the microenvironment of the polymer. Such fluorophores include acridine orange:

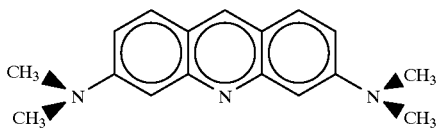

and rhodamine dyes:

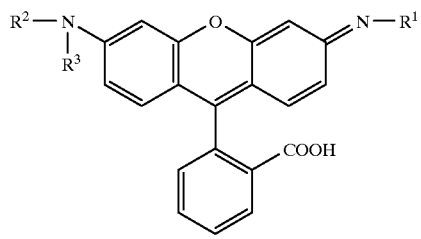

wherein $R^1$ and $R^2$ are independently an alkyl having between about 2 and 20 carbon atoms and $R^3$ is hydrogen or an alkyl having between about 2 and 20 carbon atoms. Acridine orange and rhodamine dyes are preferred fluorophores. The modulation of the acridine fluorescence is generally measured with an excitation at 489 nm and emission at 540 nm, but can be excited at other wavelengths. A ratiometric readout can be achieved by exciting at two wavelengths and generating a ratio of the two emissions as a function of ammonia. The modulation of fluorescence of a rhodamine derivative, wherein $R^1$ and $R^2$ are both $C_{18}H_{37}$, is generally measured with an excitation at 530 nm and emission at 590 nm.

Hydrophobic polymers useful in the present invention for the transducer membrane are preferably polymers in which the fluorophore is at least partially soluble. Such polymers include but are not limited to: polystyrene, polyurethane, poly(ethyl cellulose), polydienes such as poly(1,3-butadiene), butadiene-acrylonitrile copolymer, poly (dimethylbutadiene), and polyisoprene, polyalkenes such as polyethylene, isobutane-isoprene copolymer, poly(4-methylpentene), polypropylene, polyethylmethacrylate, polytetrafluoroethylene, poly(vinyl alcohol), poly(vinyl chloride), and polyoxymethylene, cellulose and cellulose derivatives, such as cellulose hydrate, cellulose acetate, cellulose nitrate, ethyl cellulose, and cellulose ethyl methacrylate, polymethacrylates such as poly(methyl methacrylate) and poly(ethyl methacrylate) as well as polysiloxanes, polyesters and polycarbonates. A preferred polymer is ethyl cellulose. These polymers may be used in both the transducing layer and the protective layer of the preferred embodiment.

The fluorophore and hydrophobic polymer are combined to form a fluorescent polymer. The signal intensities of the fluorescent polymer are high as the dye is very soluble in the organic media of the polymer, and no quenching of fluorescence occurs (as in U.S. Pat. No. 5,506,148) due to the lack of negative charges on the dye molecule. Upon exposure to ammonia, the fluorescence of the fluorescent polymer decreases, consistent with the dye becoming deprotonated with the formation of ammonium ion in the fluorescent polymer. This sensor response is reversible when the source of ammonia is withdrawn, and the ammonia in the sensor diffuses out of the membrane.

An onium compound can optionally be added to the fluorescent polymer. The onium compound adjusts the microenvironment pH of the fluorescent polymer to enhance the sensitivity to ammonia. Onium compounds include ammonium, phosphonium and pyridinium compounds. Examples of suitable onium compounds include tetrabutylammonium hydroxide, tetrabutylammonium chloride, cetyltrimethylammonium bromide, tetrabutylammonium hydrogen sulfate, tetrabutylammonium trifluoromethane, tetrabutylammonium acetate, tetraethylammonium bromide, tetraethylammonium p-toluenesulphoate, phenyltrimethylammonium chloride, benzyltrimethylammonium bromide, tetra-n-propylammonium bromide, benzyltriethylammonium tetrafluoroborate, n-dodecyltrimethylammonium bromide, tetraphenylphosphonium chloride, n-hexadecylpyridinium bromide, triphenyl phosphonium chloride, tetrabutylphosphonium bromide and hexadecyltrimethylammonium hydroxide. Preferred onium compounds are quaternary ammonium compounds, such as tetrabutylammonium hydroxide.

The sensor material can be prepared by dissolving the fluorophore and polymer in a suitable solvent, such as an alcohol, toluene, tetrahydrofuran or other organic solvent known in the art for dissolving the hydrophobic polymer. In general, the amount of fluorophore to be used should be between about 0.05% and 0.5% of the total mass. The fluorophore is preferably uniformly distributed throughout the resulting fluorescent polymer.

A membrane or film can then be formed from the dissolved fluorescent polymer by any suitable method known in the art, such as spincoating or brushing onto a non-reactive substrate, such as glass, plastic or ceramic. Alternatively, the fluorophore can be covalently attached to the polymer, as described in U.S. Pat. No. 5,005,572.

The enzyme layer is comprised of the enzyme creatinine deiminase dissolved in a hydrophilic or hydrophobic polymer, which is then deposited onto the transducer layer. The enzyme layer can be deposited onto the transducer layer in a manner similar to depositing the transducer layer on the substrate. The polymer may be crosslinked and the enzyme may be chemically modified for attachment to the polymer. Polymers useful for the enzyme layer include polyvinylalcohol, polyhydroxybutylacrylate, hydroxypropylcellulose, acrylamide derivatives, and other hydrophilic and hydrophobic polymers known to those of skill in the art.

The protective layer is comprised of a polymer which is permeable to the analyte while not being rapidly soluble in the sample matrix. The polymer can be dissolved in a solvent, which is then deposited on the enzyme layer in a similar manner. Polymers suitable for use in the protective layer are generally those polymers described above, preferably polyhydroxyethylmethacrylate (polyHEMA). This polymer is applied as a protective coating to prevent the enzyme from immediately dissolving into the sample.

The fluorescent polymers can also be used as transducer coatings for optical sensors. Traditional optical sensors for $CO_2$, $NH_3$, and other species detected via a pH modulated transducer are based on the Severinghaus model (Severinghaus, J. W.; Bradley, A. F. J. *Appl. Physiol.*, 13: 515 (1958)) where one has a transducer layer containing a pH sensitive fluorophore or chromophore, coated with a hydrophobic cover membrane material, such as a siloxane based polymer (Munkholm, C., Walt, D. R., Milanovich, F. P., *Talanta*, 35:109–112 (1988)). A difficulty inherent with Severinghaus sensors is their potential to fail due to pinhole leaks in the cover membrane. Sensors prepared by the instant invention will provide quantitative measurements of ammonia levels via a modulation of the microenvironment of the fluorophore. Since these sensor microenvironments are dispersed throughout the polymer, preparing such a sensor requires only a single application of the membrane material, and this single membrane configuration makes the problem of pinhole leaks irrelevant. The sensors are not responsive to changes in the bulk pH, indicating that the transducer microdomains are sequestered from the sample. This sensor can be used in a system which measures reflected surface fluorescence as well as in a system measuring an evanescent wave signal.

An advantage of optical sensors is their ability to resolve information from different analytes via their discrete wavebands. In this way one could couple an ammonia sensor together with a sensor for a different analyte in the same membrane, but collect the readout information at separate wavelengths. The sensor microdomains would be populated by multiple transducers but the chemistry and signal processing would be conducted as if the sensors were in separate layers. In such a multiple-analyte sensor, the transducer for the non-ammonia analyte may be a polyanionic dye, such as those described in U.S. Pat. No. 5,506,148.

The sensor material can be used as a coating on any surface and used to measure creatinine in any solution, such as in blood, saliva, or urine. It could be part of products and systems used in the measurement of critical blood analytes, in applications used to monitor dialysis, and in all clinical point of care monitoring of creatinine. It is conceivable that this sensor material could be employed in academic research projects, as it could be adapted to a variety of measuring systems, such as optical fibers.

Using the methods of this invention one can prepare extremely thin sensor films, approximately 0.5 to 5 $\mu$m thick, having a detectable level of fluorescence. Such thin films can provide an unusually rapid response time and be ideal for coating planar sensors used in evanescent wave methods of detection where one wants a fluorescent coating to be within the same dimensions as the propagating wave. Sensors prepared with this method will not be affected by pinhole leaks as the sensor material is continuous in the coating. These sensor films may also have a longer shelflife due to their lack of an aqueous layer, which would be susceptible to dehydration.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 2:
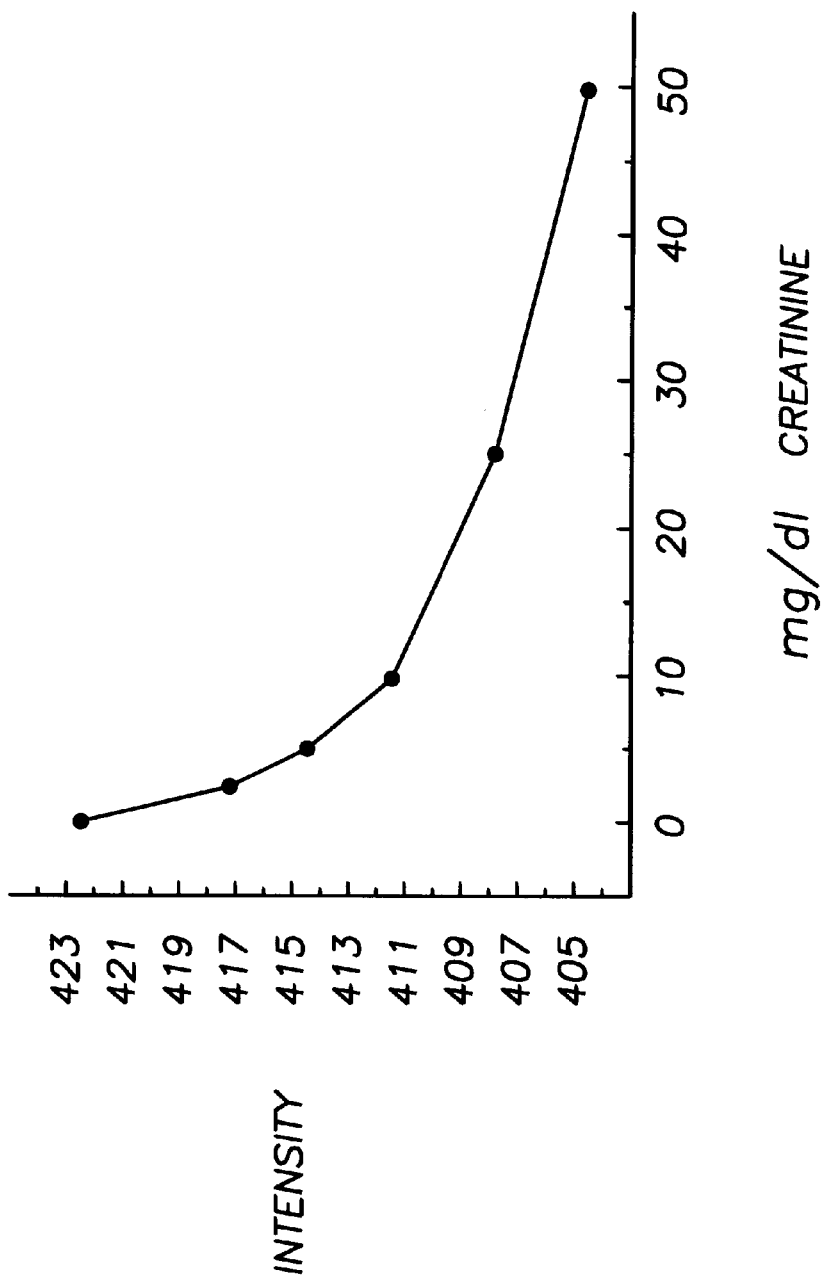
FIG. 2 shows the response of a creatinine sensor, in units of fluorescence intensity, as a function of mg/dl creatinine concentration.

The dye acridine orange was added to a 10% solution of ethyl cellulose to give $5\times10^{-4}$ M. Tetrabutylammonium hydroxide was added to give a final solution of 0.0045 M. The solution was sonicated until mixing was complete. It was then spincoated onto a glass substrate and cured in ambient conditions for 24 hours. A 5% solution of polyvinylalcohol in deionized water was prepared, using polyvinylalcohol of M.W. 124,000–186,000. The enzyme coating was prepared by adding 1 mg creatinine deiminase (Sigma, activity: 25–50 units per mg protein) to 0.15 ml polyvinylalcohol, and then applied to the ethyl cellulose layer by spincoating. A third coating of polyHEMA (10% in methanol) was applied to the enzyme layer by spincoating. (FIG. 1 shows the sensor configuration.) The sensor was cured in ambient conditions for 24 hours. It was then tested with a commercial fluorimeter, equipped with a mount for the sensor, using solutions of freshly prepared creatinine (2–50 mg/dl) in phosphate buffer, (0.05 M, pH 7.8). FIG. 2 shows the response curve of the creatinine sensor, in units of fluorescence intensity, vs. concentration of creatinine in mg/dl. The signal decreased as the concentration of creatinine increased, which is consistent with the deprotonation of acridine orange by the production of ammonia from the enzyme catalyzed hydrolysis of creatinine.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compostions and methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A creatinine sensor material comprising:
   a first layer comprising a pH-sensitive fluorophore immobilized non-aqueously within a first, hydrophobic polymer, wherein the fluorophore is protonated within the first hydrophobic polymer, can react quantitatively with ammonia, and has a transducing moiety that is neutrally charged when deprotonated;
   a second layer comprising creatinine deiminase and a second polymer, a first side of the second layer contacting one side of the first layer; and
   a third layer comprising a third polymer, the third layer contacting a second side of the second layer.

2. The sensor material of claim 1 wherein the first layer further comprises an onium compound.

3. The sensor material of claim 2 wherein the onium compound is a quaternary ammonium compound.

4. The sensor material of claim 2 wherein the onium compound is tetrabutylammonium hydroxide.

5. The sensor material of claim 1 wherein the fluorophore is acridine orange.

6. The sensor material of claim 1 wherein the fluorophore is a rhodamine dye.

7. The sensor material of claim 1 wherein the first hydrophobic polymer is ethyl cellulose.

8. The sensor material of claim 1 wherein the polymer of the second layer is polyvinyl alcohol.

9. The sensor material of claim 1 wherein the third polymer is polyhydroxyethylmethacrylate.

10. A method for measuring the concentration of creatinine, comprising:
    measuring a fluorescence of the sensor material of any of claims 1–9,
    exposing the sensor material to a solution comprising creatinine,
    measuring the fluorescence of the sensormaterial after the exposing step,
    determining a flourescene change, and
    determining the concentration of the creatinine from the fluorescene change.

11. A process for preparing a creatinine sensor material comprising:
    non-aqueously combining a pH-sensitive fluorophore and a first, hydrophobic polymer to form a first mixture, wherein the fluorophore is protonated within the first, hydrophobic polymer, can react quantitatively with ammonia, and has a transducing moiety that is neutrally charged when deprotonated;
    forming a first layer of the first mixture on a substrate;
    combining creatinine deiminase and a second polymer to form a second mixture;
    forming a second layer of the second mixture on the first layer; and
    forming a third layer of a third polymer on the second layer.

12. The process of claim 11 wherein the combining of the fluorophore and the first hydrophobic polymer is performed in the presence of a solvent.

13. The process of claim 11 wherein the fluorophore is acridine orange.

14. The process of claim 11 wherein the fluorophore is a rhodamine dye.

15. The process of claim 11 wherein the first hydrophobic polymer is ethyl cellulose.

16. The process of claim 11 wherein the polymer of the second layer is polyvinyl alcohol.

17. The process of claim 11 wherein the polymer of the third layer is polyhydroxyethylmethacrylate.

18. The process of claim 11 wherein the substrate is glass, plastic or ceramic.

19. The process of claim 11 wherein the first mixture further comprises an onium compound.

20. The process of claim 19 wherein the onium compound is a quaternary ammonium compound.

21. The process of claim 19 wherein the onium compound is tetrabutylammonium hydroxide.

22. An optical sensing device for measuring ammonia concentration in a solution comprising creatinine comprising:
    a first layer comprising a pH-sensitive fluorophore immobilized non-aqueously in a first, hydrophobic polymer, wherein the fluorophore is protonated within the first, hydrophobic polymer, can react quantitatively with ammonia, and has a transducing moiety that is neutrally charged when deprotonated, a first side of the first layer contacting a surface of an optical component, which is transparent to incident and emissive electromagnetic waves;
    a second layer comprising a creatinine deiminase and a second polymer, a first side of the second layer contacting a second side of the first layer;
    a third layer comprising a third polymer, one side of the third layer contacting a second side of the second layer;
    wherein the optical component is optically connected to means for collecting radiant emission to measure the fluorescence indicative of ammonia concentration.

23. The device of claim 22 wherein the fluorophore is acridine orange.

24. The device of claim 22 wherein the fluorophore is a rhodamine dye.

25. The device of claim 22 wherein the first, hydrophobic polymer is ethyl cellulose.

26. The device of claim 22 wherein the polymer of the second layer is polyvinyl alcohol.

27. The device of claim 22 wherein the third polymer is polyhydroxyethylmethacrylate.

28. The device of claim 22 wherein the optical component is an optical fiber.

29. The device of claim 22 wherein the optical component is a planar waveguide.

30. The device of claim 22 wherein the optical component is an evanescent wave sensor.

31. The device of claim 22 further comprising one or more sensors capable of detecting analytes other than ammonia.

32. A creatinine sensor material comprising:
    a first layer consisting essentially of a pH-sensitive fluorophore immobilized non-aqueously within a first, hydrophobic polymer, wherein the fluorophore is protonated within the first, hydrophobic polymer, can react quantitatively with ammonia, and has a transducing moiety that is neutrally charged when deprotonated;
    a second layer comprising creatinine deiminase and a second polymer, a first side of the second layer contacting one side of the first layer; and
    a third layer comprising a third polymer, the third layer contacting a second side of the second layer.

33. A creatinine sensor material comprising:
    a first layer consisting essentially of a pH-sensitive fluorophore and an onium compound immobilized non-aqueously within a first, hydrophobic polymer, wherein the fluorophore is protonated within the first, hydrophobic polymer, can react quantitatively with ammonia, and has a transducing moiety that is neutrally charged when deprotonated;
    a second layer comprising creatinine deiminase and a second polymer, a first side of the second layer contacting one side of the first layer; and
    a third layer comprising a third polymer, the third layer contacting a second side of the second layer.

34. An optical sensing device for measuring ammonia concentration in a solution comprising creatinine, comprising the creatinine sensor material of claim 32 or 33, deposited on a surface of an optical component that is transparent to incident and emissive electromagnetic waves.

* * * * *